United States Patent
Suzuki et al.

(10) Patent No.: US 6,428,804 B1
(45) Date of Patent: Aug. 6, 2002

(54) INTRA-ARTICULAR PREPARATION FOR THE TREATMENT OF ARTHROPATHY

(75) Inventors: Makoto Suzuki, Sakura; Kenji Ishigaki, Chiba; Minoru Okada, Inzai; Kenji Ono, Sakura; Shuichi Kasai, Narita; Katsumi Imamori, Yotsukaido, all of (JP)

(73) Assignee: SSP Co., Ltd., Tokyo (JP)

( * ) Notice: Subject to any disclaimer, the term of this patent is extended or adjusted under 35 U.S.C. 154(b) by 51 days.

(21) Appl. No.: 09/706,762

(22) Filed: Nov. 7, 2000

Related U.S. Application Data (63) Continuation of application No. 09/172,271, filed on Oct. 14, 1998.

(30) Foreign Application Priority Data

Oct. 27, 1997 (JP) ............................................. 9-294009

(51) Int. Cl.[7] ............................ A61F 2/00; A61F 13/00; F61K 9/14
(52) U.S. Cl. ........................ 424/426; 424/422; 424/423; 424/489; 514/825
(58) Field of Search ............................... 424/426, 489, 424/422, 423

(56) References Cited

U.S. PATENT DOCUMENTS

| | | | |
|---|---|---|---|
| 4,937,254 A | * | 6/1990 | Sheffield et al. |
| 5,061,492 A | | 10/1991 | Okada et al. ................ 424/423 |
| 5,320,824 A | | 6/1994 | Brodack et al. ............ 424/1.37 |
| 5,403,573 A | | 4/1995 | Day et al. ................... 424/1.29 |

FOREIGN PATENT DOCUMENTS

| | | | |
|---|---|---|---|
| EP | 0 102 265 | * | 3/1984 |
| EP | 0 400 522 | | 12/1990 |
| EP | 0 442 671 | | 8/1991 |
| WO | WO 91/17744 | * | 11/1991 |

OTHER PUBLICATIONS

Derwent Abstracts, AN 92–316444, AU 9181794, Aug. 1992.

Derwent Abstract, AN 85–099097, BE 900810, Apr. 1985.

\* cited by examiner

*Primary Examiner*—Thurman K. Page
*Assistant Examiner*—Isis Ghali
(74) *Attorney, Agent, or Firm*—Oblon, Spivak, McClelland, Maier & Neustadt, P.C.

(57) ABSTRACT

This invention relates to an intra-articular preparation for the treatment of arthropathy, which comprises microcapsules of (a) a high-molecular substance, which has biodegradability and biocompatibility, and (b) a drug. When applied directly to a joint area, this preparation can achieve a high drug concentration at the target area, can inhibit occurrence of general side effect, and can maintain drug efficacy over a long term. The preparation can therefore alleviate the burden on the patient.

9 Claims, 7 Drawing Sheets

# INTRA-ARTICULAR PREPARATION FOR THE TREATMENT OF ARTHROPATHY

This application is a continuation of U.S. application Ser. No. 09/172,271, filed Oct. 14, 1998.

TECHNICAL FIELD

This invention relates to an intra-articular preparation for the treatment of arthropathy, and more specifically to a microcapsule-type intra-articular preparation for the treatment of arthropathy, which is incorporated in the synovium or its peripheral tissue within a joint and gradually releases a drug over a long term.

BACKGROUND ART

As therapeutics for arthropathy such as arthritis and articular rheumatism, steroid agents, nonsteroidal antiphlogistics, antirheumatics, articular function improvers and the like are available these days. They are generally used in unit dosage forms such as capsules, tablets, powders or injections.

Since these capsules, tablets and powders are orally administered, substantial time is however required until the drug reaches a joint area. Moreover, the drug is allowed to migrate only in a small amount to the joint area so that a large dose is needed to exhibit the efficacy of the drug. Problems of general side effects have therefore been indicated. An injection, on the other hand, is applied directly to a joint area, thereby making it possible to increase the concentration of the drug at the joint area. Nonetheless, the drug so injected is generally quickly eliminated from the joint area, so that no drug efficacy can be expected to remain over a long term (for example, from one day to several months or so). If injection is made more frequently to maintain the efficacy of the drug,. substantial burden, discomfort or pain is experienced by the patient. Such frequent injection is hence not preferred.

With the foregoing in view, the present invention has as an object the provision of a dosage-form preparation for the treatment of arthropathy, which, when applied directly to a joint area, can achieve a high drug concentration at the target area, can inhibit occurrence of general side effects, can maintain drug efficacy over a long term, and can alleviate the burden on the patient.

DISCLOSURE OF THE INVENTION

With a view to achieving the above-described object, the present inventors have proceeded with extensive research. As a result, it has been found that administration of a preparation, said preparation comprising microcapsules of (a) a biodegradable, biocompatible high-molecular substance and (b) a drug, into a joint makes it possible to increase the concentration of the drug at a target area in the joint, avoid occurrence of general side effects, and permit gradual release of the drug from the preparation and hence maintain the efficacy of the drug over a long term, leading to the completion of the present invention.

The present invention therefore provides an intra-articular preparation for the treatment of arthropathy, which comprises microcapsules of (a) a high-molecular substance, which has biodegradability and biocompatibility, and (b) a drug.

BEST MODE FOR CARRYING OUT THE INVENTION

The term "microcapsules" as used herein means particles obtained by coating particles of a drug with a high-molecular substance which rather easily degrades within the living body (biodegradability) and does not give deleterious effect to the living body (biocompatibility); or particles obtained by dispersing a drug in a dissolved form or as microcrystals in such a high-molecular substance as a carrier (i.e., a polymer matrix).

Examples of the high-molecular substance having biodegradability and biocompatibility can be homopolymers and copolymers of lactic acid, glycolic acid, caprolactone, valerolactone, butyrolactone, amino acids, alkyl cyanoacrylates and hydroxybutyrates; albumin; gelatin; starch, casein; and chitosan. Preferred examples of the high-molecular substance having biodegradability and biocompatibility can be homopolymers and copolymers of lactic acid, glycolic acid, caprolactone, valerolactone, butyrolactone, amino acids, alkyl cyanoacrylates and hydroxybutyrates; and starch. These high-molecular substances can be used either singly or in combination. The above-described high-molecular substances are preferred, because they have biodegradability and biocompatibility, they permit easy coating, dissolution or dispersion of a drug, and they also permit easy control of the release rate of the drug within a joint. Among these, a homopolymer or copolymer of one or more monomers selected from the group consisting of lactic acid, glycolic acid, caprolactone, valerolactone and butyrolactone is more preferred for its non-enzymatic hydrolyzability. Particularly preferred is a copolymer of polylactic acid or lactic acid and glycolic acid. The most preferred molar ratio of lactic acid to glycolic acid in the copolymer of polylactic acid or lactic acid and glycolic acid ranges from 100/0 to 50/50.

Further, the release rate of the drug at the joint area can be controlled by adjusting the molecular weight of the high-molecular substance. The molecular weight (weight average molecular weight) of the high-molecular substance may range preferably from 10,000 to 245,000, with a range of from 10,000 to 58,000 being particularly preferred, although it varies depending on the term during which the drug is released. The proportion of the high-molecular substance in the intra-articular preparation for the treatment of arthropathy may range preferably from 20 to 99 wt. %, with a range of from 80 to 99 wt. % being particularly preferred.

No particular limitation is imposed on the drug for use in the present invention, insofar as it is generally used as a therapeutic for arthropathy. Illustrative are steroid agents, nonsteroidal anti-inflammatory drugs, antirheumatics, immunoregulators, immunosuppressors, articular function improvers, and interleukin production inhibitors. Specific examples can include dexamethasone, hydrocortisone, triamcinolone, betamethasone, predonisolone, methylpredonisolone, halopredone, beclomethasone, deprodone, diclofenac, indomethacin, ibuprofen, ketoprofen, aspirin, diflunisal, fulfenamic acid, floctafenine, tolfenamic acid, sulindac, fenbufen, salicylic acid, acemetacin, proglumetacin, nabumetone, protizinic acid, thiaprofen, oxaprozin, loxoprofen, alminoprofen, zaltoprofen, flurbiprofen, flurbiprofen axetil, piroxicam, tenoxicam, ampiroxicam, meloxicam, D-penicillamine, bucillamine, gold sodium thiomalate, auranofin, lobenzarit, salazosulfapyridine, methotrexate, cyclophosphamide, azathioprine, mizoribine, cyclosporin and hyaluronic acid; and salts thereof. They can be used either singly or in combination.

To use the drug in a suspended system, the preferred average particle size of the drug may range from 0.1 to 10 $\mu$m. This average particle size range of from 0.1 to 10 $\mu$m makes it possible to easily control the release rate of the drug within the joint. To use the drug in a solution, on the other hand, it is only necessary to dissolve the drug in a solvent of the water system or organic solvent system. The drug can be microencapsulated even if it is in a liquid form at room temperature.

The content of the drug in the intra-articular preparation according to the present invention for the treatment of arthropathy may range preferably from 1 to 80 wt. %, more preferably from 1 to 60 wt. %, notably from 1 to 20 wt. %. The content range of from 1 to 80 wt. % permits easy control of the release rate of the drug, so that the efficacy of the drug can be maintained over a long term.

It is necessary for the intra-articular preparation according to the present invention for the treatment of arthropath that it is allowed to adhere on or is incorporated in the synovium or its peripheral tissue within a joint. The uptake of the intra-articular preparation according to the present invention on or in the synovium or its peripheral tissue decreases with the p article size while an excessively small particle size makes it difficult to control the release rate, although these trends differ depending on the properties and efficacy of the drug. Therefore the average particle size may range preferably from 5 to 530 $\mu$m, more preferably from 5 to 260 $\mu$m. To increase the uptake into the joint, it is particularly preferred to control the average particle size within a range of from 20 to 123 $\mu$m, with a range of from 20 to 58 $\mu$m being extremely preferred.

No particular limitation is imposed on the preparation method of the intra-articular preparation according to the present invention for the treatment of arthropathy, which preparation comprises microcapsules. Depending on the properties of the intended intra-articular preparation for the treatment of arthropathy, solvent evaporation, solvent extraction, phase separation, spray coating, spray drying, submerged hardening coating, interfacial polymerization or the like can be used. Described specifically, an intra-articular preparation can be prepared, for example, by the method to be described next. First, a high-molecular substance is dissolved in a solvent. To the resulting solution, a drug is then added for dissolution or suspension. Here, the drug may be added in the form of an aqueous solution or as a solution in an organic solvent. The thus-obtained solution or suspension is added to an aqueous solution which may contain a surfactant or a protective colloid as needed, and the resulting mixture is agitated or otherwise processed into an emulsion. The solvent in the emulsion is then caused to evaporate. By subsequent agitation, collection by filtration, drying, sifting and the like as needed, an intra-articular preparation for the treatment of arthropathy, said preparation being composed of microcapsules, can be obtained. Incidentally, the intra-articular preparation according to the present invention for the treatment of arthropathy can be obtained in an aseptic form. Namely, the intra-articular preparation can be aseptically obtained by producing it in a sterilized room while using germ-free raw materials and sterilized equipment. Further, even a preparation produced in a non-aseptic form can be supplied in an aseptic form by exposing it to ultraviolet rays or the like and sterilizing the same.

For the intra-articular preparation according to the present invention for the treatment of arthropathy, use in the form of an injection is particularly preferred. When employed as an injection, the intra-articular preparation for the treatment of arthropathy can be administered by suspending it in a dispersion medium for microcapsules. As the dispersion medium for microcapsules, injection-grade water may be used. Further, a suspending agent, a stabilizer, a buffer, a preservative, a thickening agent, an isotonicity and/or the like can be added as needed. It is particularly preferred to use a microcapsule-dispersing medium which contains one or more compounds selected from the group consisting of hyaluronic acid, chondroitin sulfate and salts thereof. The use of such a dispersion medium makes it possible to minimize irritation to the joint, which tends to occur as a result of administration.

The present invention will next be described in further detail by the following examples. It should however be borne in mind that the present invention shall not be limited to or by the following examples.

EXAMPLES 1-5

Preparation of Beclomethasone-propionate-containing Microcapsule Samples of Different Particle Sizes A lactic acid-glycolic acid copolymer (PLGA; co-monomer molar ratio: 50/50, weight average molecular weight: 57,600) (4.5 g) was dissolved in methylene chloride (40.5 g) to prepare a 10% solution. Beclomethasone propionate (0.5 g) was added to and dissolved in the thus-prepared solution. The resulting solution was added to a 0.5% aqueous polyvinyl alcohol solution (100 g) which had been prepared in advance. The mixture so obtained was agitated for 1 minute by a marine propeller stirrer, whereby an O/W-type emulsion was formed. The emulsion was added under stirring to a 0.5% aqueous polyvinyl alcohol solution (300 g). The methylene chloride in the emulsion was caused to evaporate so that microencapsulation was conducted. Subsequent to stirring at 37° C. for 120 minutes, microcapsules were collected by filtration, dried under reduced pressure and then sifted. By changing conditions for the stirring as desired, beclomethasone-propionate-containing microcapsule samples having the drug contents and particle sizes shown in Table 1 were obtained.

TABLE 1

|  | Drug content (%) | Minimum particle size ($\mu$m) | Maximum particle size ($\mu$m) | Average particle size ($\mu$m) |
| --- | --- | --- | --- | --- |
| Example 1 | 10.2 | 3.9 | 42.6 | 20.7 |
| Example 2 | 9.3 | 18.3 | 120.2 | 57.5 |
| Example 3 | 9.0 | 42.6 | 225.6 | 122.7 |
| Example 4 | 8.8 | 168.4 | 351.0 | 261.4 |
| Example 5 | 8.8 | 442.2 | 612.3 | 530.6 |

Test 1

Pharmacokinetic Test of Beclomethasone-propionate-containing Microcapsule Samples of Different Particle Sizes.

Figure 1:
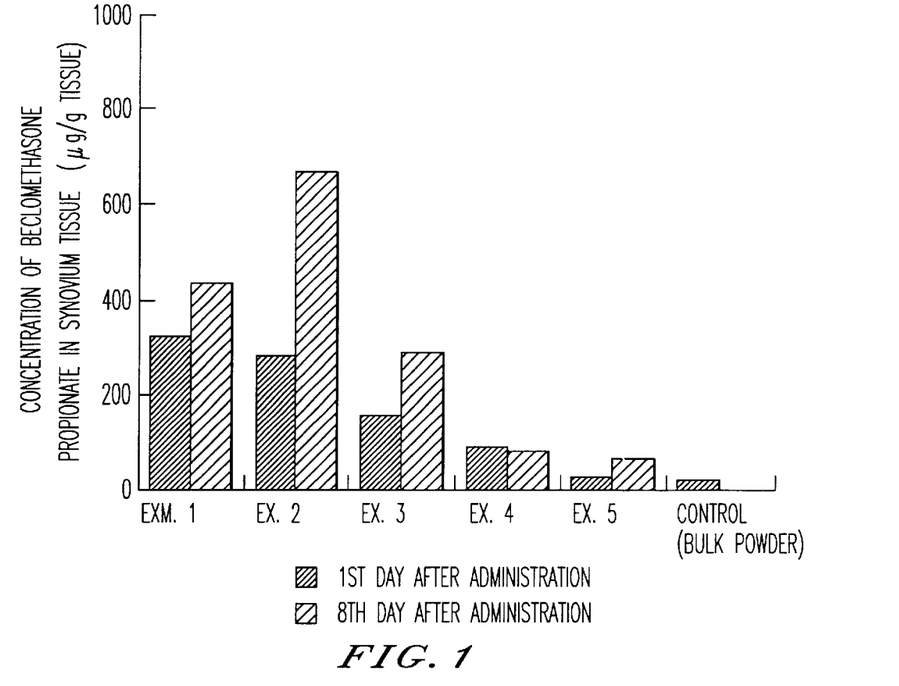
FIG. 1 is a graph showing the amounts of beclomethasone propionate in synoviums and their peripheral tissues when beclomethasone-propionate-containing microcapsules and bulk powder of beclomethasone propionate were administered into knee joints of rabbits, respectively.

The microcapsule samples obtained in Examples 1–5 were separately suspended in an injection-grade dispersion medium (which was composed of injection-grade water, an isotonicity, a suspending agent and the like). The resulting suspensions were injected in a dose of 1 mg in terms of beclomethasone propionate into knee joints of rabbits, respectively. As a control, bulk powder of beclomethasone propionate (average particle size: 0.38 $\mu$m) was suspended in the above-described injection-grade dispersion medium and was injected in a similar manner as described above. On the 1st and 8th days after the administration, the amounts of beclomethasone propionate in the synoviums and their peripheral tissues were determined. The results are shown in FIG. 1. On the 1st day after the administration, substantially no beclomethasone propionate had migrated into the synovium and its peripheral tissue when the bulk powder was used (the control). In the case of the microcapsule samples of Examples 1–4, on the other hand, the migrated amounts were greater compared with the control. On the 8th day after the administration, greater migrated amounts were observed in Examples 1–5 compared with the control. Especially in each of Examples 1–3, beclomethasone propionate was confirmed to remain in a substantial amount in the synovium and its peripheral tissue.

EXAMPLE 6

Preparation of Predonisolone-containing microcapsules by Spray Drying

PLGA (comonomer molar ratio: 50/50, weight average molecular weight: 124,000) (2.5 g) and predonisolone (0.278 g) were dissolved in methylene chloride (347.2 g). The resulting solution was sprayed in a spray granulator ("YAMATO MINI-SPRAY Model DL-21"), whereby microcapsules were obtained. The microcapsules had a predonisolone content of 10.1% and an average particle size of 5.61 $\mu$m.

Test 2

Release Test of Predonisolone-containing Microcapsules

Figure 2:
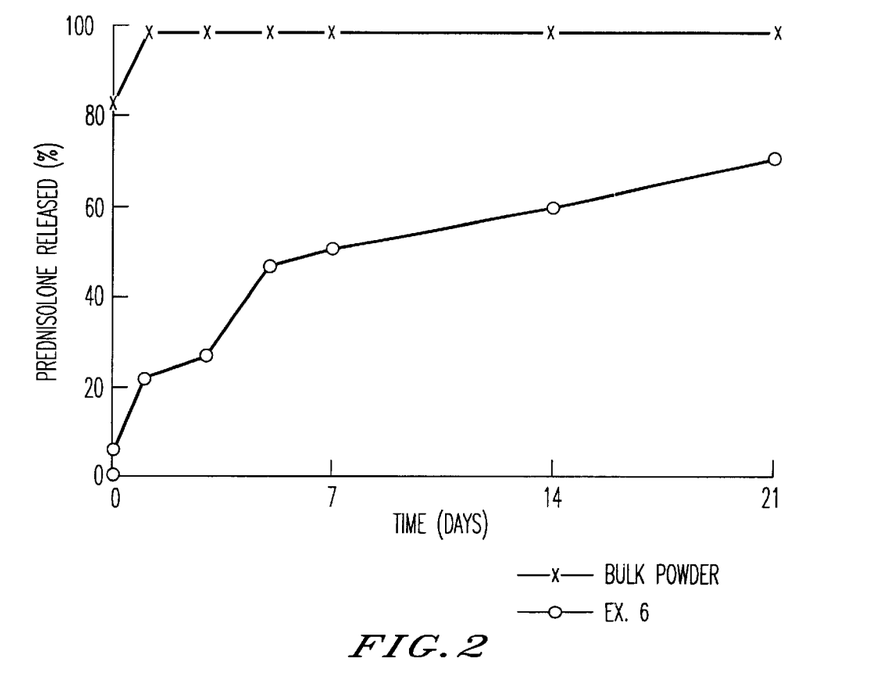
FIG. 2 is a graph illustrating a release profile of predonisolone from predonisolone-containing microcapsules, which had been prepared by spray drying, into a phosphate buffer of pH 6.8.

The predonisolone-containing microcapsules obtained in Example 6 (as much as 0.5 mg in terms of predonisolone) and bulk powder of predonisolone (0.5 mg) were placed in 10-ml aliquots of a phosphate buffer of pH 6.8, respectively, and the dissolved amounts were measured periodically. The results are shown in FIG. 2.

From the results, it has been found that the release of predonisolone from predonisolone-containing microcapsules is delayed compared with that of predonisolone from bulk powder of predonisolone.

EXAMPLES 7–13

Preparation of Microcapsule Samples Containing Dexamethasone Sodium Phosphate at Different Contents Dexamethasone-sodium-phosphate-containing microcapsule samples were prepared by using their materials in the amounts shown in Table 2. Described specifically, each microcapsule sample of its corresponding dexamethasone sodium phosphate (DXNa) content shown in Table 2 was obtained in the manner to be described next. PLGA (comonomer molar ratio: 50/50, weight average molecular weight: 57,600) was dissolved in methylene chloride to provide a 20% solution. DXNa (average particle size: 2.50 $\mu$m) was added to and suspended in the solution. The resulting suspension was added to an aqueous solution (38.2 g) which had been prepared in advance and which contained polyvinyl alcohol (1.57%) and calcium chloride (27.0%). The thus-obtained mixture was agitated by a marine propeller stirrer for 1 minute, whereby an O/W-type emulsion was formed. The emulsion was added under stirring to purified water (3.3 l). The methylene chloride in the emulsion was extracted and caused to evaporate, whereby microencapsulation was conducted. Subsequent to stirring for 30 minutes, the resulting microcapsules were sifted to collect those having particle sizes in a range of from 45 to 250 $\mu$m, and the thus-collected microcapsules were dried under reduced pressure.

TABLE 2

| | Amount of PLGA (g) | Amount of methylene chloride (g) | Amount of DXNa (g) | Content of DXNa (%) |
|---|---|---|---|---|
| Example 7 | 4.87 | 19.48 | 0.13 | 1.1 |
| Example 8 | 4.75 | 19.00 | 0.25 | 3.8 |
| Example 9 | 4.50 | 18.00 | 0.5 | 9.3 |
| Example 10 | 4.00 | 16.00 | 1.0 | 17.0 |
| Example 11 | 3.00 | 12.00 | 2.0 | 27.3 |
| Example 12 | 2.00 | 8.00 | 3.0 | 46.6 |
| Example 13 | 1.00 | 4.00 | 4.0 | 77.8 |

EXAMPLES 14–18

Preparation of DXNa-containing Microcapsule Samples with PLGAs of Different Molecular Weights In each example, PLGA having the corresponding weight average molecular weight shown in Table 3 (comonomer molar ratio: 50/50) (4.75 g) was dissolved in methylene chloride (42.75 g) to provide a 10% solution. DXNa (0.25 g) was added to and suspended in the solution. The suspension was added to an aqueous solution (76.4 g) which had been prepared in advance and which contained polyvinyl alcohol (1.57%) and calcium chloride (27.0%). The thus-obtained mixture was agitated by a marine propeller stirrer for 1 minute, whereby an O/W-type emulsion was formed. The emulsion was added under stirring to purified water (6.6 l). In a similar manner as in Examples 7–13, DXNa-containing microcapsules having the corresponding DXNa content (W/W%) and average particle size shown in Table 3 were obtained.

TABLE 3

| | Molecular weight | Average particle size (μm) | Cotent of DXNa (%) |
|---|---|---|---|
| Example 14 | 10,000 | 102.5 | 3.3 |
| Example 15 | 57,600 | 76.6 | 4.4 |
| Example 16 | 124,000 | 94.6 | 4.4 |
| Example 17 | 157,000 | 120.6 | 3.7 |
| Example 18 | 245,000 | 109.9 | 4.1 |

EXAMPLES 19–21

Preparation of DXNa-containing Microcapsules with PLGAs of Different Comonomer Molar Ratios In each example, PLGA having the corresponding comonomer molar ratio shown in Table 4 (weight average molecular weight: approximately 100,000) (4.75 g) was dissolved in methylene chloride (42.75 g) to provide a 10% solution. DXNa (0.25 g) was added to and suspended in the solution. Procedures were then conducted as in Examples 14–18, whereby DXNa-containing microcapsules having the corresponding DXNa content (W/W%) and average particle size shown in Table 4 were obtained.

TABLE 4

| | Comonomer molar ratio (lactic acid/glycolic acid) | Average particle size (μm) | Content of DXNa (%) |
|---|---|---|---|
| Example 19 | 50/50 | 80.5 | 4.2 |
| Example 20 | 75/25 | 102.5 | 4.6 |
| Example 21 | 100/0 | 98.6 | 4.2 |

Test 3

Release Test of DXNa-containing Microcapsule Samples

Figure 3:
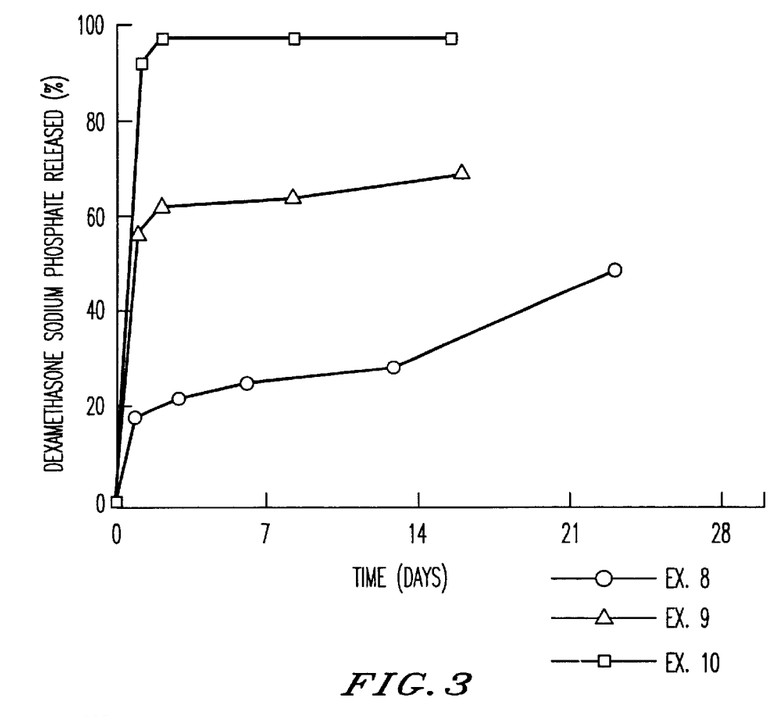
FIG. 3 is a graph showing release profiles of dexamethasone sodium phosphate from microcapsule samples of different dexamethasone sodium phosphate contents into a phosphate buffer of pH 7.5.
Figure 4:
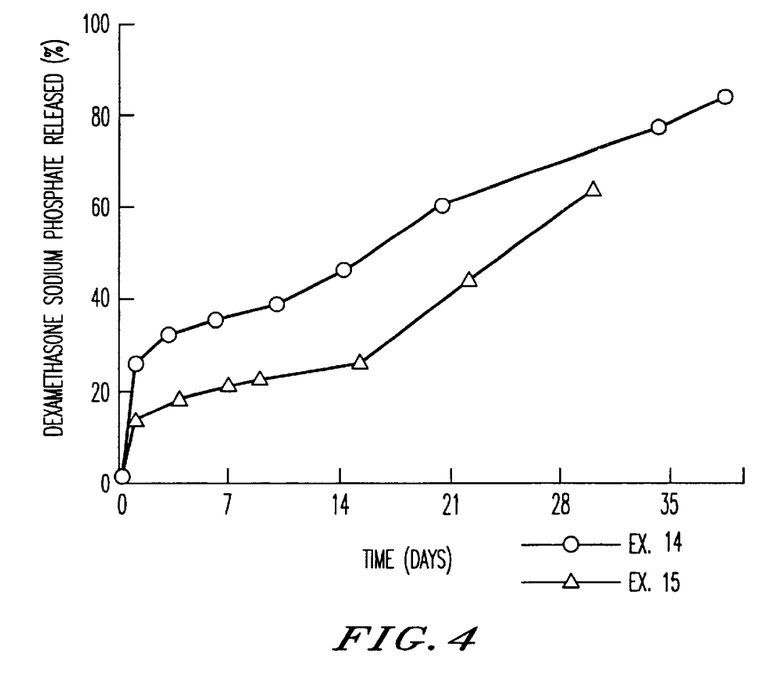
FIG. 4 is a graph depicting release profiles of dexamethasone sodium phosphate from dexamethasone-sodium-phosphate-containing microcapsule samples, which had been formed using lactic acid-glycolic acid copolymers of different molecular weights, respectively, into a phosphate buffer of pH 7.5.
Figure 5:
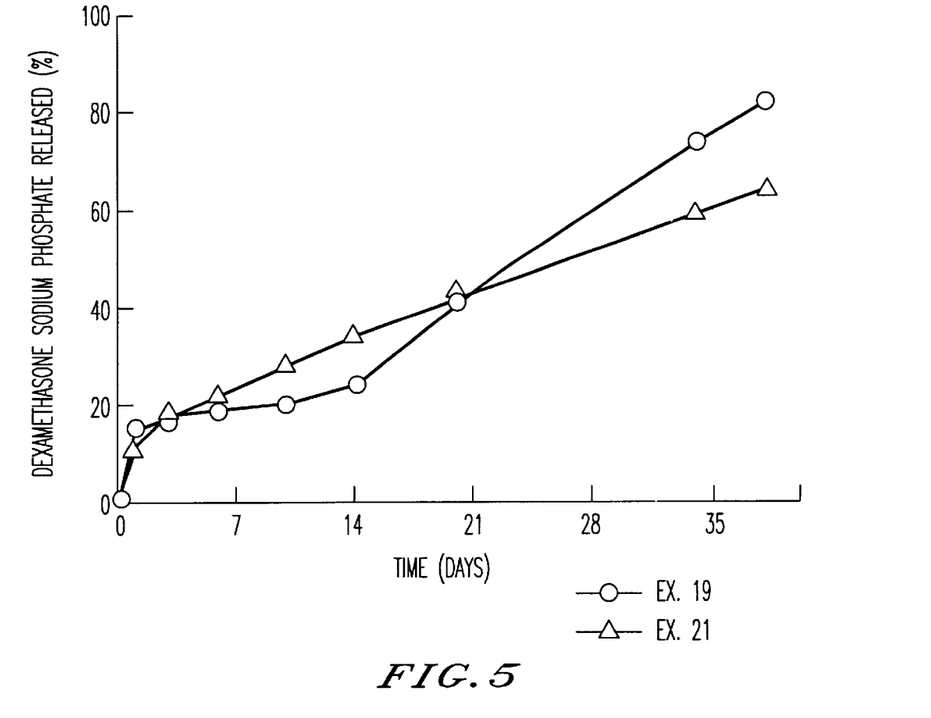
FIG. 5 is a graph depicting release profiles of dexamethasone sodium phosphate from dexamethasone-sodium-phosphate-containing microcapsule samples, which had been formed using lactic acid-glycolic acid copolymers of different comonomer molar ratios, respectively, into a phosphate buffer of pH 7.5.

The DXNa-containing microcapsule samples obtained in Examples 8, 9, 10, 14, 15, 19 and 21 (as much as 2 mg in terms of DXNa) were added to 10-ml aliquots of a phosphate buffer of pH 7.5, respectively, and the dissolved amounts were measured periodically. The results are shown in FIG. 3, FIG. 4 and FIG. 5. From FIG. 3 to FIG. 5, it has been confirmed that the release rate of DXNa as a drug can be controlled by varying at least one of the content of DXNa in microcapsules, which are available by submerged drying in a water system, and the molecular weight and comonomer molar ratio of PLGA.

Test 4

Pharmacokinetic Test of DXNa-containing Microcapsules

Figure 6:
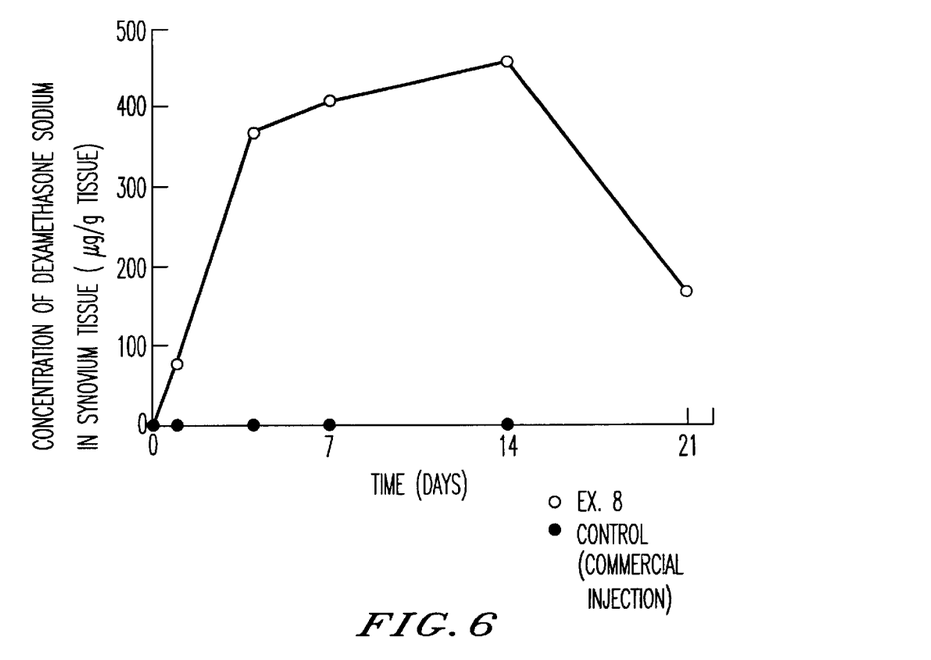
FIG. 6 is a graph showing the amounts of dexamethasone sodium phosphate in synoviums and their peripheral tissues when dexamethasone-sodium-propionate-containing microcapsules and a commercial injection of dexamethasone sodium phosphate were administered into knee joints of rabbits, respectively.

The DXNa-containing microcapsules (average particle size: 70.8 μm) obtained in Example 8 were suspended in the same injection-grade dispersion medium as that employed in Test 1. The resulting suspension was administered in a dose of 9 mg in terms of dexamethasone into a knee joint of a rabbit, and the amount of DXNa in the synovium and its peripheral tissue was measured. As a control, a commercial injection (an aqueous solution in an amount as much as 3 mg in terms of dexamethasone) was administered. The results are shown in FIG. 6. When the commercial injection was used, no existence of DXNa was observed in the synovium and its peripheral tissue. In the case of the DXNa-containing microcapsules of Example 8, on the other hand, DXNa remained over a long term. It has hence been confirmed that, when administered intra-articularly, DXNa-containing microcapsules are allowed to adhere on or are incorporated in the synovium and its peripheral tissue and DXNa is released and allowed to remain over a long term.

EXAMPLES 22–24

Preparation of Capsules Containing Diclofenac Sodium at Different Contents

In each example, PLGA shown in Table 5 (comonomer molar ratio: 50/50, weight average molecular weight: 178,000) was dissolved in acetone to provide a 5% solution (6° C.). The corresponding diclofenac sodium (DFNa, average particle size: 1.85 μm) shown in Table 5 was added to and dissolved in the solution. The resulting solution was added to liquid paraffin (70 g) which had been controlled at 6° C. The resulting mixture was agitated for 30 seconds by a marine propeller stirrer, whereby an emulsion was formed. The emulsion was added under stirring to liquid paraffin (1.5 kg), followed by stirring for 3 hours. During the stirring, the temperature of the liquid mixture was caused to gradually rise from 6° C. to 50° C., whereby the acetone in the emulsion was extracted and caused to evaporate so that microencapsulation was conducted. After the resulting microcapsules were sifted to collect those having particle sizes in a range of from 45 to 250 μm, the thus-collected microcapsules were repeatedly washed with hexane. Subsequent to drying under reduced pressure, DFNa-containing microcapsules having the corresponding DFNa content (W/W %) and average particle size shown in Table 5 were obtained.

TABLE 5

|  | Amount of PLGA (g) | Amount acetone (g) | Amount of DFNa (g) | Content of DFNa (%) | Average particle size (μm) |
|---|---|---|---|---|---|
| Example 22 | 1.0 | 19.0 | 0.1 | 6.5 | 89.9 |
| Example 23 | 1.0 | 19.0 | 0.2 | 10.4 | 63.8 |
| Example 24 | 1.0 | 19.0 | 0.4 | 17.5 | 79.1 |

EXAMPLE 25

Preparation of DFNa-containing Microcapsules

PLGA (comonomer molar ratio: 50/50, weight average molecular weight: 178,000) (4.5 g) was dissolved in methylene chloride (40.5 g) to provide a 10% solution. DFNa (average particle size: 1.85 μm, 0.5 g) was added to and suspended in the solution. The suspension was added to an aqueous solution (76.4 g) which had been prepared in advance and which contained polyvinyl alcohol (1.57%) and calcium chloride (27.0%). The thus-obtained mixture was agitated by a marine propeller stirrer for 1 minute, whereby an O/W-type emulsion was formed. The emulsion was added under stirring to purified water (6.6 l). The methylene chloride in the emulsion was extracted and caused to evaporate, whereby microencapsulation was conducted. After stirring for 30 minutes, sifting was conducted to collect microcapsules having particle sizes in a range of from 45 to 250 μm. The thus-collected microcapsules were dried under reduced pressure, whereby DFNa-containing microcapsules [DFNa content: 8.3% (W/W), average particle size: 67.9 μm] were obtained.

Test 5

Release Test of DFNa-containing Microcapsule Samples

Figure 7:
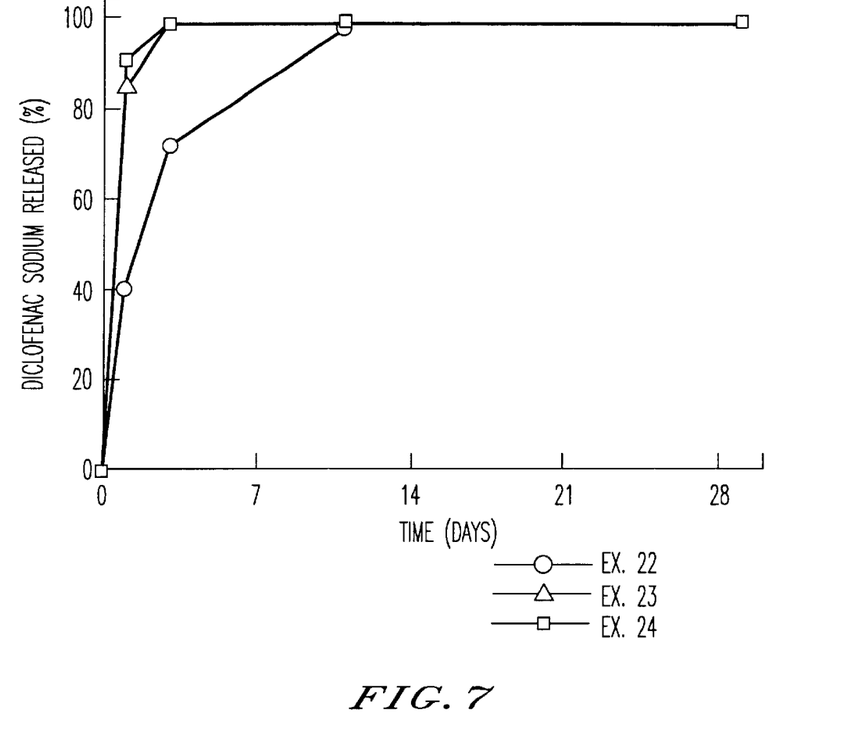
FIG. 7 is a graph showing release profiles of diclofenac sodium from microcapsule samples of different diclofenac sodium contents into a phosphate buffer of pH 7.5.
Figure 8:
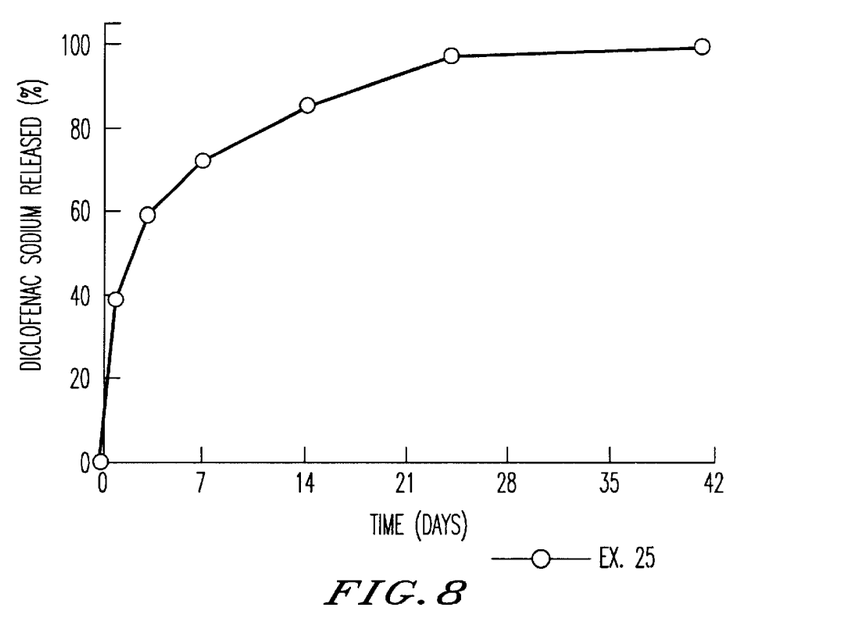
FIG. 8 is a graph illustrating a release profile of diclofenac sodium from diclofenac-sodium-containing microcapsules into a phosphate buffer of pH 7.5.

The DFNa-containing microcapsule samples obtained in Examples 22–25 (as much as 2 mg in terms of DFNa) were added to 10-ml aliquots of a phosphate buffer of pH 6.8, respectively, and the dissolved amounts were measured periodically. The results are shown in FIG. 7 and FIG. 8. From FIG. 7, it has been confirmed that the release rate of DFNa can be controlled by varying the content of DFNa in microcapsules.

Test 6

Pharmacokinetic Test of DFNa-containing Microcapsules

Figure 9:
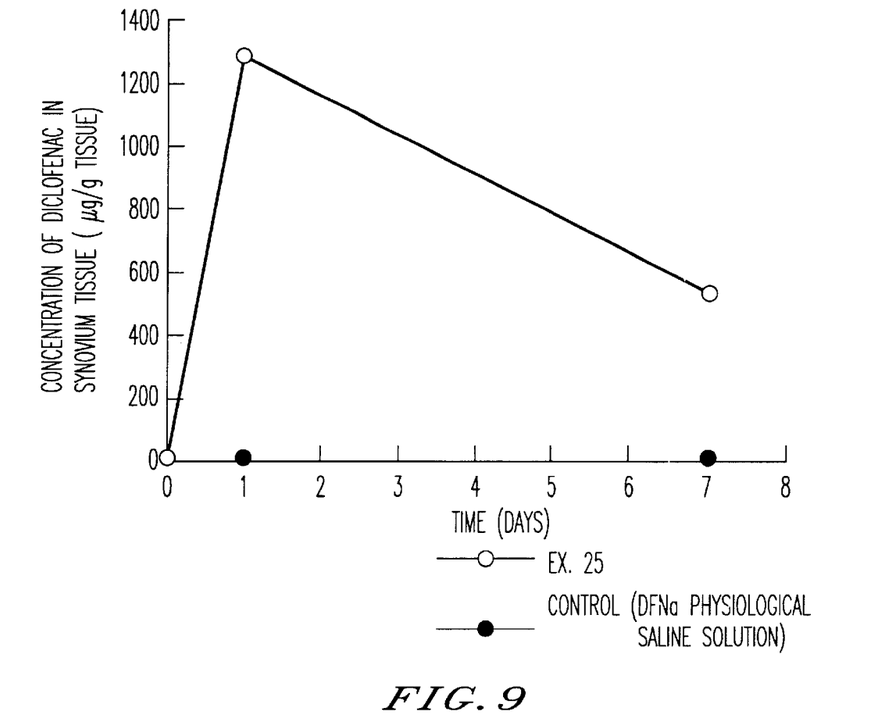
FIG. 9 is a graph illustrating the amounts of diclofenac in synoviums and their peripheral tissues when diclofenac-sodium-containing microcapsules and a solution of diclofenac sodium in a physiological saline were administered into knee joints of rabbits, respectively.

The DFNa-containing microcapsules (average particle size: 67.9 μm) obtained in Example 25 were suspended in the same injection-grade dispersion medium as that employed in Test 1. The resulting suspension was injected in a dose of 10 mg in terms of DFNa into a knee joint of a rabbit, and the amount of DF in the synovium and its peripheral tissue was measured periodically. As a control, a solution of DFNa in a physiological saline was injected in a dose of 1 mg in terms of DFNa, and measurements were conducted. The results are shown in FIG. 9. In the case of the solution of DFNa in the physiological saline, no existence of DF was observed in the synovium and its peripheral tissue. In the case of the DFNa-containing microcapsules of Example 25, on the other hand, DF remained over a long term. It has hence been confirmed that, when administered intra-articularly, DFNa-containing microcapsules are allowed to adhere on or are incorporated in the synovium and its peripheral tissue and DFNa is released and allowed to remain over a long term.

EXAMPLE 26

Preparation of Methotrexate-containing Microcapsules

PLGA (comonomer molar ratio: 50/50, weight average molecular weight: 57,600) (1.8 g) was dissolved in methylene chloride (7.2 g) to provide a 20% solution. Methotrexate (MTX, average particle size: 8.89 μm) (0.2 g) was added to and suspended in the solution. The suspension was added to an aqueous solution (13.2 g) which had been prepared in advance and which contained polyvinyl alcohol (1.57%) and calcium chloride (27.0%). The thus-obtained mixture was agitated by a marine propeller stirrer for 1 minute, whereby an O/W-type emulsion was formed. The emulsion was added under stirring to purified water (1.3 l). The methylene chloride in the emulsion was extracted and caused to evaporate, whereby microencapsulation was conducted. After stirring for 30 minutes, sifting was conducted to collect microcapsules having particle sizes in a range of from 45 to 250 μm. The thus-collected microcapsules were dried under reduced pressure, whereby MTX-containing microcapsules [average particle size: 65.1 μm, MTX content: 11.9% (W/W)] were obtained.

Test 7

Release Test of MTX-containing Microcapsules

Figure 10:
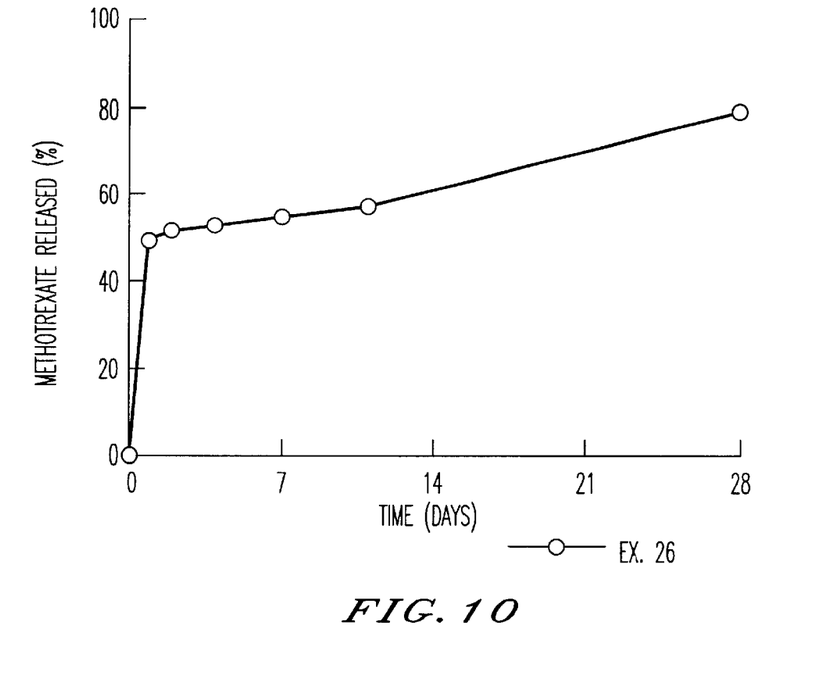
FIG. 10 is a graph depicting a release profile of methotrexate from methorexate-containing microcapsules into a phosphate buffer of pH 7.5.

The MTX-containing microcapsules obtained in Example 26 (as much as 2 mg in terms of MTX) were added to a phosphate buffer of pH 7.5 (10-ml), and the dissolved amount was measured periodically. The results are shown in FIG. 10. From FIG. 10, it was confirmed that MTX was released over a long term from the MTX-containing microcapsules of Example 26.

Test 8

Pharmacokinetic Test of MTX-containing Microcapsules

Figure 11:
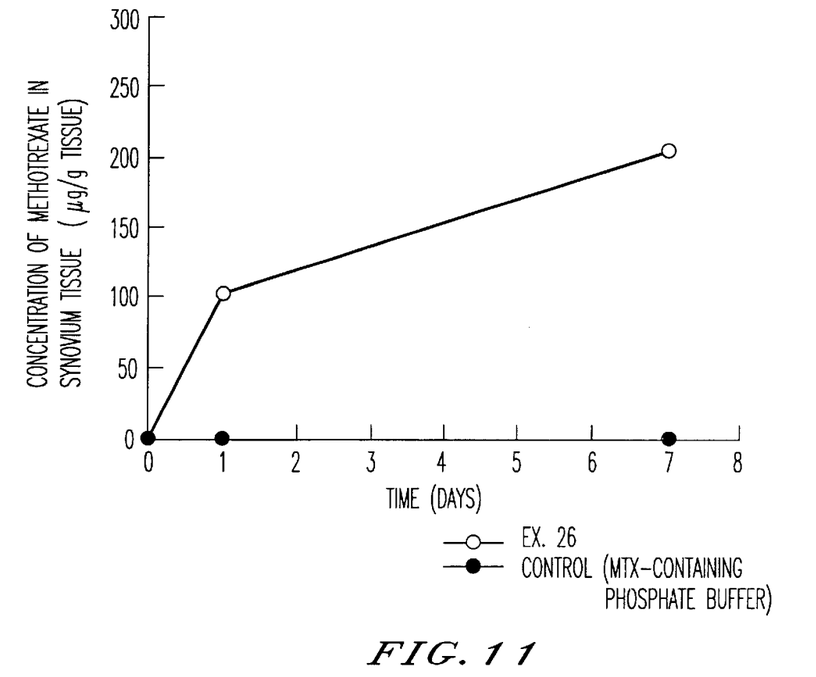
FIG. 11 is a graph depicting the amounts of methotrexate in synoviums and their peripheral tissues when methotrexate-containing microcapsules and a solution of methotrexate in a phosphate buffer of pH 7.5 were administered into knee joints of rabbits, respectively.

The MTX-containing microcapsules obtained in Example 26 were suspended in the same injection-grade dispersion medium as that employed in Test 1. The resulting suspension was injected in a dose of 1 mg in terms of MTX into a knee joint of a rabbit, and the amount of MTX in the synovium and its peripheral tissue was measured periodically. As a control, MTX was dissolved in a phosphate buffer of pH 7.5 and the resulting solution was injected in a dose of 1 mg in terms of MTX. The results are shown in FIG. 11. In the case of the solution of MTX in the phosphate buffer, no existence of MTX was observed in the synovium and its peripheral tissue. In the case of the MTX-containing microcapsules of Example 26, on the other hand, MTX remained over a long term. It has hence been confirmed that, when administered intra-articularly, MTX-containing microcapsules are allowed to adhere on or are incorporated in the synovium and its peripheral tissue and MTX is released and allowed to remain over a long term.

EXAMPLE 27

Preparation of Cyclophosphamide-containing Microcapsules

PLGA (comonomer molar ratio: 50/50, weight average molecular weight: 57,600) (3.2 g) was dissolved in methylene chloride (13.2 g) to provide a 20% solution. Cyclophosphamide (0.8 g) was added to and dissolved in the solution. The solution was added to an aqueous solution (23.2 g) which had been prepared in advance and which contained polyvinyl alcohol (1.57%) and calcium chloride (27.0%). The thus-obtained mixture was agitated by a marine propeller stirrer for 1 minute, whereby an O/W-type emulsion was formed. The emulsion was added under stirring to purified water (2.6 l). The methylene chloride in the emulsion was extracted into a water phase and caused to evaporate, whereby microencapsulation was conducted. After stirring for 30 minutes, sifting was conducted to collect microcapsules having particle sizes in a range of from 45 to 250 μm. The thus-collected microcapsules were dried under reduced pressure, whereby cyclophosphamide-containing microcapsules [cyclophosphamide content: 17.2% (W/W)] were obtained.

Test 9

Pharmacokinetic Test of Cyclophosphamide-containing Microcapsules

Figure 12:
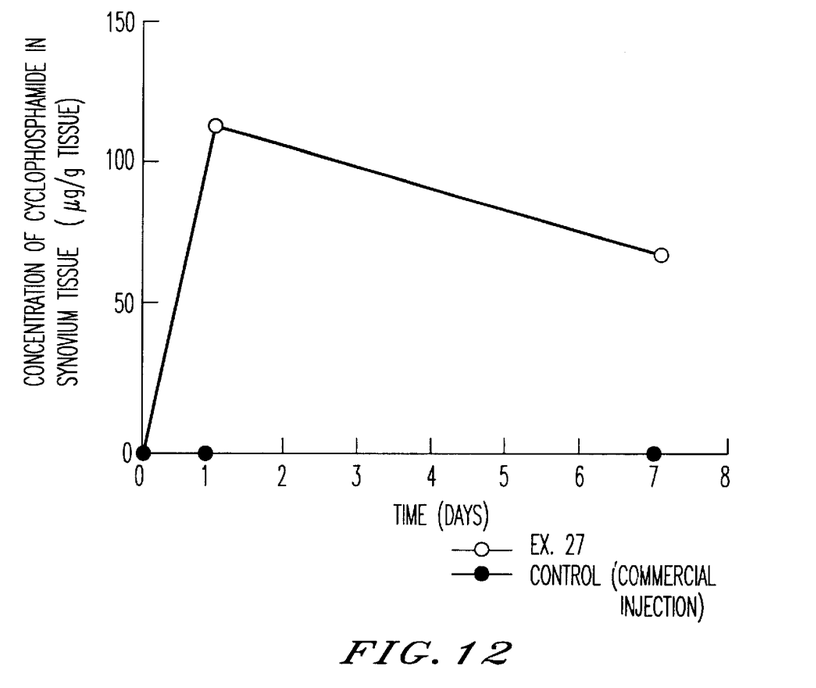
FIG. 12 is a graph showing the amounts of cyclophosphamide in synoviums and their peripheral tissues when cyclophosphamide-containing microcapsules and a commercial injection of cyclophosphamide were administered into knee joints of rabbits, respectively.

The cyclophosphamide-containing microcapsules obtained in Example 27 were suspended in the same injection-grade dispersion medium as that employed in Test 1. The resulting suspension was administered in a dose of 10 mg in terms of cyclophosphamide into a knee joint of a rabbit, and the amount of cyclophosphamide in the synovium and its peripheral tissue was measured. As a control, a commercial injection (an aqueous solution in an amount as much as 10 mg in terms of cyclophosphamide) was administered likewise. The results are shown in FIG. 12. In the case of the commercial injection of cyclophosphamide, no existence of cyclophosphamide was observed in the synovium and its peripheral tissue. In the case of the cyclophosphamide-containing microcapsules of Example 27, on the other hand, cyclophosphamide remained over a long term. It has hence been confirmed that, when administered intra-articularly, cyclophosphamide-containing microcapsules are allowed to adhere on or are incorporated in the synovium and its peripheral tissue and cyclophosphamide is released and allowed to remain over a long term.

EXAMPLE 28

Preparation of D-penicillamine-containing Microcapsules

PLGA (comonomer molar ratio: 50/50, weight average molecular weight: 57,600) (3.2 g) was dissolved in methylene chloride (13.2 g) to provide a 20% solution. D-penicillamine (0.8 g) was added to and suspended in the solution. The suspension was added to an aqueous solution (23.2 g) which had been prepared in advance and which contained polyvinyl alcohol (1.57%) and calcium chloride (27.0%). The thus-obtained mixture was agitated by a marine propeller stirrer for 1 minute, whereby an O/W-type emulsion was formed. The emulsion was added under stirring to purified water (2.6 l). The methylene chloride in the emulsion was extracted into a water phase and caused to evaporate, whereby microencapsulation was conducted. After stirring for 30 minutes, sifting was conducted to collect microcapsules having particle sizes in a range of from 45 to 250 mm. The thus-collected microcapsules were dried under reduced pressure, whereby D-penicillamine-containing microcapsules [D-penicillamine content: 16.3% (W/W)] were obtained.

EXAMPLE 29

Preparation of sodium-hyaluronate-containing Microcapsules

PLGA (comonomer molar ratio: 50/50, weight average molecular weight: 178,000) (4.5 g) was dissolved in methylene chloride (40.5 g). In the resulting solution, pulverized sodium hyaluronate (viscosity average molecular weight: approximately 1,000,000, average particle size: 5.08 μm) (500 mg) was uniformly suspended. The hyaluronic acid suspension was added to an aqueous solution (76.4 g) of polyvinyl alcohol and calcium chloride (concentration of polyvinyl alcohol: 1.57%, concentration of calcium chloride: 27.0%) while agitating the aqueous solution at 1,000 rpm by a marine propeller stirrer, so that the suspension was emulsified. The emulsion was then added to purified water (6.6 l) while stirring the latter at 700 rpm by a marine propeller stirrer. The resulting mixture was stirred for 30 minutes, whereby microcapsules were formed. The microcapsules were collected by filtration, washed with purified water and then dried, whereby hyaluronic-acid-containing microcapsules were obtained. The thus-obtained microcapsules were in the form of powder having an average particle size of 80 μm and a sodium hyaluronate content of 5.8% (W/W).

EXAMPLE 30

Preparation of Microcapsules Containing Fluorescence-labeled Sodium Hyaluronate

Microcapsules were obtained in a similar manner as in Example 29 by using sodium hyaluronate (viscosity average molecular weight: approximately 1,000,000, average particle size: 5.01 μm) which had been labeled with a fluorescent substance (fluorescamine) for its distinction from sodium hyaluronate existing in the living body. As PLGA, one having a comonomer molar ratio of 50/50 and a weight average molecular weight of 10,000 was used. The microcapsules were prepared so that the content of the fluorescence-labeled hyaluronic acid became 10% (W/W) as a theoretical value. The actual content of the fluorescence-labeled hyaluronic acid was 7.3% (W/W).

EXAMPLE 31

Preparation of Microcapsules Containing Fluorescence-labeled Sodium Hyaluronate

PLGA (comonomer molar ratio: 50/50, weight average molecular weight: 57,600) (0.9 g) was dissolved in acetone (12 g). In the resulting solution, pulverized sodium hyaluronate (viscosity average molecular weight: approximately 1,000,000, average particle size: 5.01 μm) (600 mg) was uniformly suspended. The suspension was added to liquid paraffin (70 g) while agitating the liquid paraffin at 1,500 rpm and 6° C. by a marine propeller stirrer, so that the suspension was emulsified. The emulsion was then added to liquid paraffin (1,500 g) while stirring the latter at 800 rpm and 35° C. by a marine propeller stirrer. The resulting mixture was stirred for 60 minutes, whereby microcapsules were formed. The microcapsules were collected by filtration, washed with n-hexane and then dried, whereby microcapsules containing fluorescence labeled hyaluronic acid were obtained. The thus-obtained microcapsules were in the form of powder having an average particle size of 40 μm, and the content of the fluorescence-labeled sodium hyaluronate was 40.2% (W/W).

Test 10

Figure 13:
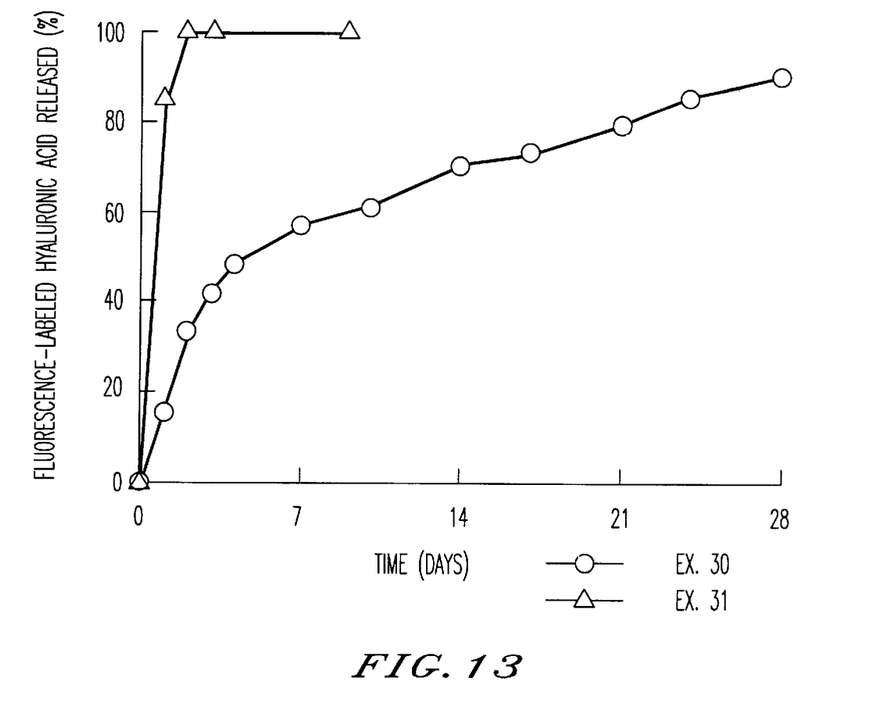
FIG. 13 is a graph depicting release profiles of fluorescence-labeled hyaluroic acid from microcapsule samples, which contained fluorescence-labeled hyaluroic acid and had been formed using lactic acid-glycolic acid copolymers of different molecular weights, respectively, into water.

Release Test of Microcapsule Samples Containing Fluorescence-labeled Sodium Hyaluronate The microcapsule samples obtained in Examples 30 and 31 (as much as 2 mg in terms of fluorescence-labeled hyaluronic acid) were added to 3-ml aliquots of purified water, respectively, and the dissolved amounts were measured periodically. The results are shown in FIG. 13. As a result, it has been suggested that microcapsules having a lower content of fluorescence-labeled hyaluronic acid is slower in release.

Figure 14:
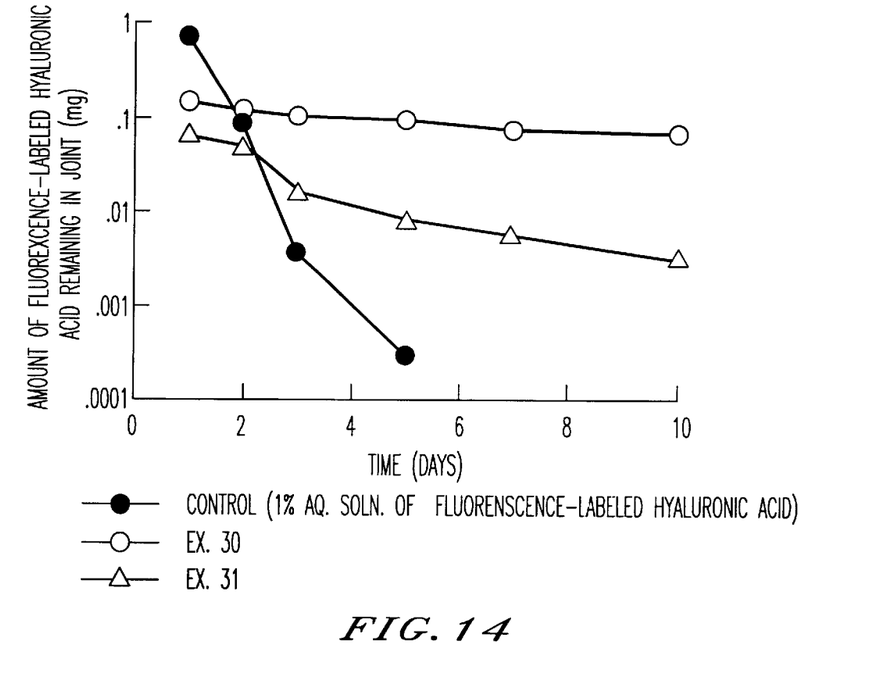
FIG. 14 is a graph showing the amounts of fluorescence-labeled hyaluronic acid remaining in knee joints of rabbits when an aqueous solution of fluorescence-labeled hyaluronic acid and microcapsule samples containing fluorescence-labeled hyaluronic acid were administered to the knee joints.

Test 11
Pharmacokinetic Test of Microcapsule Samples Containing Fluorescence-labeled Sodium Hyaluronate The microsphere samples (6 mg), which had been prepared in Examples 30 and 31, were suspended in aliquots of the same injection-grade dispersion medium as that employed in Test 1. The resulting suspensions were administered into knee joints of rabbits, respectively. The fluorescence-labeled hyaluronic acid remaining in each knee joint was periodically quantitated to determine the in vivo residence property of the drug. As a control, an aqueous solution (1.0% W/V, 3 mg) of fluorescence-labeled hyaluronic acid was administered. The results are shown in FIG. 14. Compared with the aqueous solution of fluorescence-labeled hyaluronic acid, the administration of the microcapsule samples with fluorescence-labeled hyaluronic acid contained therein resulted in the maintenance of fluorescence-labeled hyaluronic acid within the knee joints. When the microcapsule samples containing fluorescence-labeled hyaluronic acid, said samples featuring slow in vitro release, were administered, the fluorescence-labeled hyaluronic acid remained over a still longer term. Microspheres with hyaluronic acid contained therein have therefore been confirmed to permit control of its in vivo duration time by controlling of the release of hyaluronic acid.

EXAMPLE 32

Preparation of Gelatin Microcapsules Containing Dexamethasone Acetate

Gelatin (3.3 g) was added to purified water (10 ml) and was then dissolved at 70° C. Dexamethasone acetate (0.37 g) was added to and thoroughly dispersed in the resultant solution. The dispersion was then added to liquid paraffin (200 ml) which had been heated to 70° C. beforehand. The resulting mixture was agitated for 5 minutes by a marine propeller stirrer so that an emulsion was formed. The emulsion, while being stirred by the marine propeller stirrer, was allowed to cool down to 5° C., whereby microcapsules were formed. After stirring for 30 minutes, the microcapsules were collected by filtration and washed with n-hexane. They were dried, whereby microcapsules were obtained.

EXAMPLE 33

Preparation of Flurbiprofen-containing Microcapsules

PLGA (comonomer molar ratio: 50/50, weight average molecular weight: 57,600) (2.25 g) was dissolved in methylene chloride (20.25 g) to provide a 10% solution. Flurbiprofen (0.25 g) was added to and dissolved in the solution. The solution was added to a 1% aqueous polyvinyl alcohol solution (67 g) which had been prepared in advance. The thus-obtained mixture was agitated by a marine propeller stirrer for 1 minute, whereby an O/W-type emulsion was formed. The emulsion was added under stirring to purified water (3,750 g). The methylene chloride in the emulsion was extracted and caused to evaporate, whereby microencapsulation was conducted. After stirring at 25° C. for 30 minutes and then at 35° C. for 60 minutes, sifting was conducted to collect microcapsules having particle sizes in a range of from 45 to 250 μm. The thus-collected microcapsules were dried under reduced pressure, whereby flurbiprofen-containing microcapsules [flurbiprofen content: 8.2% (W/W)] were obtained.

EXAMPLE 34

Preparation of Flurbiprofen-akisechiru-containing Microcapsules

PLGA (comonomer molar ratio: 50/50, weight average molecular weight: 57,600) (2.25 g) was dissolved in methylene chloride (20.25 g) to provide a 10% solution. Flurbiprofen akisechiru (0.25 g) was added to and dissolved in the solution. The solution was added to a 1% aqueous polyvinyl alcohol solution (67 g) which had been prepared in advance. The thus-obtained mixture was agitated by a marine propeller stirrer for 1 minute, whereby an O/W-type emulsion was formed. The emulsion was added under stirring to purified water (3,750 g). The methylene chloride in the emulsion was extracted and caused to evaporate, whereby microencapsulation was conducted. After stirring at 25° C. for 30 minutes and then at 35° C. for 60 minutes, sifting was conducted to collect microcapsules having particle sizes in a range of from 45 to 250 μm. The thus-collected microcapsules were dried under reduced pressure, whereby flurbiprofen-axetil-containing microcapsules [flurbiprofen axetil content: 10.3% (W/W)] were obtained.

Capability of Exploitation in Industry

When the intra-articular preparation according to the present invention for the treatment of arthropathy is administered into a joint, microcapsules with the drug contained therein are allowed to adhere on or are incorporated in the synovium and its peripheral tissue and gradually release the drug. As a consequence, the drug remains over a longer term within the joint than administration of the drug in the form of an aqueous solution. This makes it possible to maintain the efficacy of the drug for a duration time as long as needed against inflammation of the synovium tissue and also against pain and/or a reduction in the function of the joint caused by the inflammation. Further, the drug is allowed to migrate in a greater amount to the target area so that drug efficacy can be exhibited at a small dose. Induction of general side effects can therefore be avoided practically.

What is claimed is:

1. An injectable intra-articular preparation for the treatment of arthropathy, comprising microcapsules suspended in a microcapsule-dispersing medium comprising at least one compound selected from the group consisting of hyaluronic acid, chondroitin sulfate and salts thereof, wherein the microcapsules comprise (a) a high-molecular weight substance, which has biodegradability and biocompatibility, and (b) an arthropathy therapeutic drug, wherein said microcapsules have an average particle size of from 20 to 123 μm.

2. The intra-articular preparation according to claim 1, wherein said high-molecular substance is at least one biodegradable, biocompatible high-molecular substance selected from the group consisting of homopolymers and copolymers of lactic acid, glycolic acid, caprolactone, valerolactone, butyrolactone, amino acids, alkyl cyanoacrylates and hydroxybutyrates; albumin; gelatin; starch, casein; and chitosan.

3. The intra-articular preparation according to claim 1, wherein said high-molecular substance is at least one biodegradable, biocompatible high-molecular substance selected from the group consisting of homopolymers and copolymers of lactic acid, glycolic acid, caprolactone, valerolactone, butyrolactone, amino acids, alkyl cyanoacrylates and hydroxybutyrates; and starch.

4. The intra-articular preparation according to claim 1, wherein said drug is a steroid agent, nonsteroidal antiphlogistic, antirheumatic, immunoregulator, immunosuppressor or articular function improver.

5. The intra-articular preparation according to claim 1, wherein said drug is at least one drug selected from the group consisting of dexamethasone, hydrocortisone, triamcinolone, betamethasone, predonisolone, methylpredonisolone, halopredone, beclomethasone, deprodone, diclofenac, indomethacin, ibuprofen, ketoprofen, aspirin, diflunisal, fulfenamic acid, floctafenine, tolfenamic acid, sulindac, fenbufen, salicylic acid, acemetacin, proglumetacin, nabumetone, protizinic acid, thiaprofen, oxaprozin, loxoprofen, alminoprofen, zaltoprofen, flurbiprofen, flurbiprofen axetil, piroxicam, tenoxicam, ampiroxicam, meloxicam, D-penicillamine, bucillamine, gold sodium thiomalate, auranofin, lobenzarit, salazosulfapyridine, methotrexate, cyclophosphamide, azathioprine, mizoribine, cyclosporin and hyaluronic acid; and salts thereof.

6. The intra-articular preparation according to claim 1, wherein the content of said drug ranges from 1 to 80 wt. %.

7. The intra-articular preparation according to claim 1, which is in the unit dosage form of an injection.

8. The intra-articular preparation according to claim 5, wherein the drug is beclomethasone or a salt thereof.

9. The intra-articular preparation according to claim 8, wherein the drug is beclomethasone propionate.

\* \* \* \* \*